(12) United States Patent
Loo et al.

(10) Patent No.: US 12,309,954 B1
(45) Date of Patent: May 20, 2025

(54) PROTECTIVE STRUCTURES WITH INTEGRATED ELECTRICAL INTERCONNECTS FOR ACTIVE IMPLANTABLE MEDICAL DEVICES

(71) Applicant: Verily Life Sciences LLC, South San Francisco, CA (US)

(72) Inventors: Alexander Loo, Redwood City, CA (US); Ellen Kaplan, South San Francisco, CA (US)

(73) Assignee: Verily Life Sciences LLC, Dallas, TX (US)

( * ) Notice: Subject to any disclaimer, the term of this patent is extended or adjusted under 35 U.S.C. 154(b) by 847 days.

(21) Appl. No.: 17/470,565

(22) Filed: Sep. 9, 2021

Related U.S. Application Data

(60) Provisional application No. 63/076,663, filed on Sep. 10, 2020.

(51) Int. Cl.
   *H05K 5/00* (2025.01)
   *H05K 5/02* (2006.01)
   *H05K 5/10* (2025.01)

(52) U.S. Cl.
   CPC ............ *H05K 5/10* (2025.01); *H05K 5/0026* (2013.01); *H05K 5/0086* (2013.01); *H05K 5/0247* (2013.01)

(58) Field of Classification Search
   CPC .. H05K 5/0004; H05K 5/0026; H05K 5/0086; H05K 5/0217; H05K 5/0247
   See application file for complete search history.

(56) References Cited

U.S. PATENT DOCUMENTS

| | | | |
|---|---|---|---|
| 7,672,730 B2 | 3/2010 | Firlik | |
| 8,914,110 B2 | 12/2014 | He et al. | |
| 9,308,380 B2 | 4/2016 | Stevenson | |
| 9,630,352 B2 | 4/2017 | Fernandez | |
| 9,833,627 B2 * | 12/2017 | Aghassian | ........... A61N 1/3787 |
| 2004/0176816 A1 | 9/2004 | Singhal | |
| 2005/0111798 A1 * | 5/2005 | Doiron | ................... H05K 5/069 |
| | | | 385/94 |
| 2007/0060955 A1 | 3/2007 | Strother | |
| 2009/0247237 A1 * | 10/2009 | Mittleman | ............ H04M 1/026 |
| | | | 455/567 |
| 2010/0204756 A1 * | 8/2010 | Aghassian | ......... A61N 1/37217 |
| | | | 607/60 |

(Continued)

*Primary Examiner* — Sagar Shrestha
(74) *Attorney, Agent, or Firm* — Kilpatrick Townsend & Stockton LLP

(57) ABSTRACT

The present disclosure relates to implantable medical devices having protective structures with integrated electrical interconnects. Particularly, aspects of the present disclosure are directed to a medical device that includes a first nest portion and a second nest portion mateable with the first nest portion to form a nest housing. The nest housing includes an interior surface and an exterior surface with a component cavity defined by the interior surface. An electronics module is disposed within a first region of the component cavity. A power source is disposed within a second region of the component cavity. An electrical interconnect is formed on or embedded within the first nest portion, the second nest portion, or a combination thereof. The electrical interconnect electrically connects the electronics module to the power source.

20 Claims, 9 Drawing Sheets

(56) References Cited

U.S. PATENT DOCUMENTS

| | | | |
|---|---|---|---|
| 2012/0048615 A1* | 3/2012 | Masumoto | H02S 40/34 |
| | | | 174/547 |
| 2012/0101551 A1* | 4/2012 | Aghassian | A61N 1/37235 |
| | | | 29/601 |
| 2012/0123502 A1* | 5/2012 | Aghassian | A61N 1/025 |
| | | | 607/59 |
| 2014/0085839 A1* | 3/2014 | Nakano | H05K 5/061 |
| | | | 361/752 |
| 2015/0070852 A1* | 3/2015 | Kawano | H05K 7/142 |
| | | | 361/736 |
| 2015/0157862 A1* | 6/2015 | Greenberg | H05K 3/4061 |
| | | | 607/116 |
| 2016/0067502 A1 | 3/2016 | Bornzin | |
| 2016/0126154 A1* | 5/2016 | Hoehn | H01L 23/3735 |
| | | | 257/693 |
| 2016/0353563 A1* | 12/2016 | Morimoto | H05K 5/0026 |
| 2019/0328949 A1* | 10/2019 | Bluvshtein | A61N 1/3787 |
| 2020/0137910 A1* | 4/2020 | Nielsen | H05K 5/069 |
| 2023/0378788 A1* | 11/2023 | Miyauchi | G01D 5/14 |
| 2024/0114637 A1* | 4/2024 | McCurdy | H01H 35/10 |

\* cited by examiner

PROTECTIVE STRUCTURES WITH INTEGRATED ELECTRICAL INTERCONNECTS FOR ACTIVE IMPLANTABLE MEDICAL DEVICES

CROSS-REFERENCE TO RELATED APPLICATION

The present application is a non-provisional application of, and claims the benefit and priority of U.S. Provisional Application No. 63/076,663, filed Sep. 10, 2020. The contents of the aforementioned application are incorporated by reference herein in its entirety.

FIELD OF THE INVENTION

The present disclosure relates to implantable medical devices, and in particular to protective structure with integrated electrical interconnects for active implantable medical devices.

BACKGROUND

Normal neural activity is an intricate balance of electrical and chemical signals, which can be disrupted by a variety of insults (genetic, chemical or physical trauma) to the nervous system, causing cognitive, motor and sensory impairments. Similar to the way a cardiac pacemaker or defibrillator corrects heartbeat abnormalities, neuromodulation therapies help to reestablish normal neural balance. In particular instances, neuromodulation therapies utilize medical device technologies to enhance or suppress activity of the nervous system for the treatment of disease. These technologies include implantable as well as non-implantable neuromodulation devices and systems that deliver electrical, chemical or other agents to reversibly modify brain and nerve cell activity. The most common neuromodulation therapy is spinal cord stimulation to treat chronic neuropathic pain. In addition to chronic pain relief, some examples of neuromodulation therapies include deep brain stimulation for essential tremor, Parkinson's disease, dystonia, epilepsy and psychiatric disorders such as depression, obsessive compulsive disorder and Tourette syndrome; sacral nerve stimulation for pelvic disorders and incontinence; vagus nerve stimulation for rheumatoid arthritis; gastric and colonic stimulation for gastrointestinal disorders such as dysmotility or obesity; vagus nerve stimulation for epilepsy, obesity or depression; carotid artery stimulation for hypertension, and spinal cord stimulation for ischemic disorders such as angina and peripheral vascular disease.

Neuromodulation devices and systems tend to have a similar form factor, derived from their predecessors, e.g. the pacemaker or defibrillator. Such neuromodulation devices and systems typically consist of an implant comprising a neurostimulator having electronics connected to a lead assembly that delivers electrical pulses to electrodes interfaced with nerves or nerve bundles via an electrode assembly. The lead assembly is typically formed of a conductive material and takes the form of an insulated wire (e.g., a dedicated channel) connected to the electrodes via a first connector on one end (e.g., a distal end) and the electronics of the neurostimulator via a second connector on another end (e.g., a proximal end). In some instances (e.g., deep implants), the lead assembly comprises additional conductors and connectors such as extension wires or a cable connected via connectors between the electrodes and the electronics of the neurostimulator.

Conventional neuromodulation devices include an enclosure or protective structure (e.g., a hermetically sealed casing) to house multiple electronic components including a power source, pulse generator, a processor, a memory device, an integrated circuit board, an antenna, and wirings connecting the multiple electronic components together. Each of these electronic components can have its own enclosure or protective structure and rely on many different types of connectors between dissimilar materials to electrically connect the electronic components. While long-term implantable neuromodulation devices have the advantage of being in a fairly constant environment once implanted, the protective structures and electrical connections need to meet the challenges of the severity of the environment (e.g., fluids and tissue), complex loading conditions, ever increasing device-lifetime requirements, and very tight size tolerances. The design principles of protective structures and electrical connectors, namely providing encapsulation (e.g., epoxy and hermetic enclosures) of components to isolate them from the harsh biological environment while avoiding disruption of connections or device failure, must be scaled down to meet the ever decreasing device sizes. Because of the long-term reliability of printed circuit board (PCB), space saving PCB assembly strategies (e.g., automated surface-mount assembly of parts such as QFN (quad flat no-lead) or chip-scale packaging (CSP) are often employed to improve miniaturization while maintaining electrical connections via traditional means such as wave soldering, traditional soldering, or surface mount technology. Any electrical components planned for integration on the PCB or to be connected with the PCB must meet routing density and size tolerances imposed by these PCB assembly strategies. As a result, the layout of the neuromodulation devices and electronic components available for integration or connection is fairly limited. As such, the industry is constrained to relatively few design options in long-term implant applications.

BRIEF SUMMARY

In various embodiments, a medical device is provided that comprises: a first nest portion, a second nest portion mateable with the first nest portion to form a nest housing, a component cavity, an electronics module disposed within a first region of the component cavity, a power source disposed within a second region of the component cavity, and an electrical interconnect formed on or embedded within the first nest portion, the second nest portion, or a combination thereof. The nest housing comprises an interior surface and an exterior surface, the component cavity being defined by the interior surface. The electronics module comprises a processor, a pulse generator, a non-transitory machine readable storage medium, or any combination thereof. The electrical interconnect electrically connects the electronics module to the power source.

In some embodiments, the medical device further includes a first electrical contact disposed between the electrical interconnect and the electronics module, and a second electrical contact disposed between the electrical interconnect and the power source. The nest housing may provide a force on the first electrical contact and the second electrical contact to maintain electrical connection between the electronics module and the power source via the first electrical contact and the second electrical contact. The first electrical contact and the second electrical contact may be formed on or embedded within the first nest portion, the second nest portion, or a combination thereof. The first electrical contact and the second electrical contact may be a spring clip, a pogo pin, a contact pad, or a combination thereof.

In some embodiments, the medical device further includes a casing formed around the nest housing. The casing may be formed of a bioceramic, bioglass, or titanium. The medical device may further include a layer of compliant material disposed between the nest housing and the casing. The compliant material may be polyurethane, polycarbonate, silicone, polyethylene, fluoropolymer, or combinations thereof In some embodiments, the medical device further includes a cap fixed to the nest housing, and one or more feedthroughs that pass through the cap. The electronics module may be electrically connected to the one or more feedthroughs.

In some embodiments, the first nest portion, the second nest portion, or a combination thereof comprise one or more layers of dielectric material and the electrical interconnect is formed on or embedded within the one or more layers of dielectric material. The dielectric material may be a polyimide, a liquid crystal polymer (LCP), parylene, polyether ether ketone (PEEK), or a combination thereof. The electrical interconnect may comprise a conductive material and the conductive material is copper (Cu), gold (Au), silver (Ag), gold/chromium (Au/Cr), platinum (Pt), platinum/iridium (Pt/Ir), titanium (Ti), gold/titanium (Au/Ti), or any alloy thereof.

In some embodiments, the electronics module is a printed circuit board assembly (PCBA). The PCBA may be formed on one or more layers of dielectric material.

In some embodiments, the electrical interconnect is a wire, a drawn filled tube, a helical coiled conductor, a microwire, a conductive metal trace, or a printed circuit.

In some embodiments, the medical device further comprises a first fit component disposed between the first nest portion, the second nest portion, or a combination thereof and the electronics module; and a second fit component disposed between the first nest portion, the second nest portion, or a combination thereof and the power source. The first fit component and the second fit component provide force on the electronics module and the power source, respectively, to maintain electrical connection between the electronics module and the power source via the first electrical contact, the second electrical contact, and the electrical interconnect.

In some embodiments, the medical device further comprises an antenna and another electrical interconnect formed on or embedded within the one or more layers of dielectric material. The another electrical interconnect may electrically connect the antenna to the electronics module or the power source. The antenna may be a wireless charging antenna or a wireless communication antenna. The antenna may be disposed within a third region of the component cavity.

In various embodiments, a medical device is provided that comprises an implantable neurostimulator and a lead assembly. The implantable neurostimulator includes: a nest housing comprising an interior surface and an exterior surface, a component cavity defined by the interior surface, an electronics module disposed within a first region of the component cavity, where the electronics module comprises a processor and a pulse generator, a power source disposed with a second region of the component cavity, an electrical interconnect formed on or embedded within a portion of the nest housing, where the electrical interconnect electrically connects the electronics module to the power source, a cap fixed to the nest housing, and one or more feedthroughs that pass through the cap, where the electronics module is electrically connected to the one or more feedthroughs. The lead assembly includes: a lead body including a conductor material, a lead connector that connects the conductor material to the one or more feedthroughs, and one or more electrodes connected to the conductor material.

In some embodiments, the implantable neurostimulator further includes: a first electrical contact disposed between the electrical interconnect and the electronics module and a second electrical contact disposed between the electrical interconnect and the power source. The nest housing may provide a force on the first electrical contact and the second electrical contact to maintain electrical connection between the electronics module and the power source via the first electrical contact and the second electrical contact.

In some embodiments, the nest housing further includes one or more layers of dielectric material and the electrical interconnect is formed on or embedded within the one or more layers of dielectric material.

In some embodiments, the electronics module is a printed circuit board assembly (PCBA). The PCBA may be formed on one or more layers of dielectric material.

In some embodiments, the implantable neurostimulator further includes an antenna and another electrical interconnect formed on or embedded within the one or more layers of dielectric material. The another electrical interconnect may electrically connect the antenna to the electronics module or the battery. The antenna may be a wireless charging antenna or a wireless communication antenna. The antenna may be disposed within a third region of the component cavity.

In various embodiments, a medical device is provided that comprises: a nest housing comprising one or more layers of dielectric material, where the one or more layers of dielectric material form an interior surface and an exterior surface of the nest housing, a component cavity defined by the interior surface, a first electronic component disposed within the component cavity, a second electronic component disposed within the component cavity, an electrical interconnect formed on or embedded within the one or more layers of dielectric material, a first electrical contact disposed between the electrical interconnect and the first electronic component, and a second electrical contact disposed between the electrical interconnect and the second electronic component. The electrical interconnect may electrically connect the first electronic component and the second electronic component via the first electrical contact and the second electrical contact.

BRIEF DESCRIPTION OF THE DRAWINGS

The present invention will be better understood in view of the following non-limiting figures, in which.

DETAILED DESCRIPTION

I. Introduction

Figure 1:
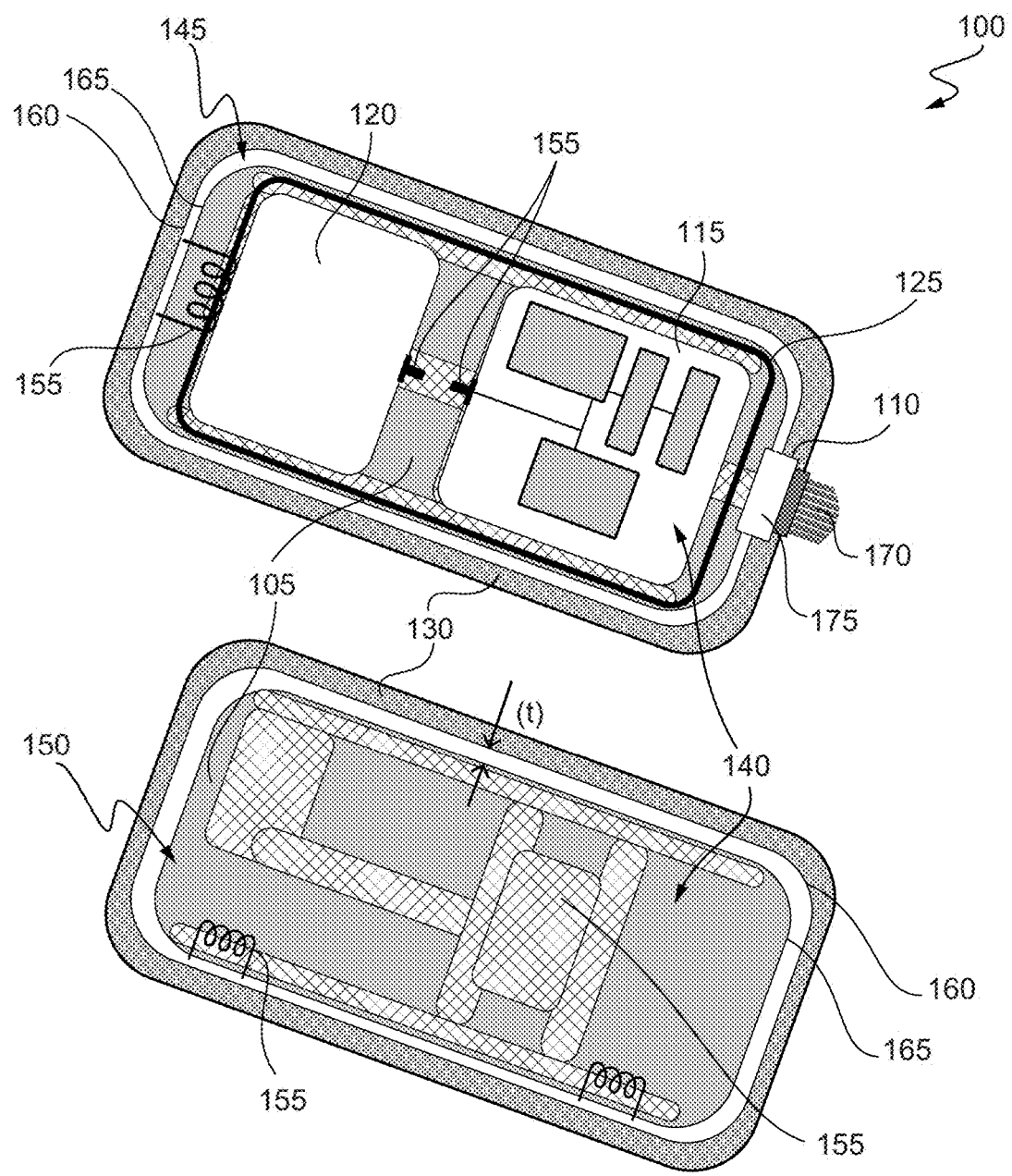
FIG. 1 shows a medical device having a nest housing in accordance with various embodiments, with the nest housing viewed from the top of two unmated portions and looking into a component cavity.

The following disclosure describes a protective housing for medical devices such as neuromodulation devices or neural control interface devices (also known as brain computer interface devices). Neuromodulation devices and neural control interface devices such as deep brain interfaces and spinal cord stimulators electrically interface with neural tissue and treat various neurological conditions through electrical stimulation and/or recording of nerve signals. Devices according to the present disclosure may include neuromodulation devices, neurostimulator devices, neural control interface devices, active implantable medical devices (AIMDs), cardiac devices, and pacing devices. As described herein, conventional neuromodulation devices or neural control interface devices employ a housing (e.g., a hermetic encapsulation) to hold a power source and an electronics module or printed circuit board assembly (PCBA) as well as other electronic components. The fabrication and size of electronic components makes utilizing more dimensionally tolerant interconnect solutions such as flex PCBs or cables, wires, crimps, terminals, plug/receptacles connectors, and routed pins not possible. Challenges for conventional medical devices in manufacturing include that the tolerances may not directly scale with the nominal dimensions. Resulting misalignment between the power source and the corresponding electronics module can result in marginal or even inoperable electrical connections. Due to scale, mechanical stresses caused by even the slightest misalignment may result in inoperability. Additionally, precisely balanced designing and fabricating of the housing is needed to sufficiently secure components within the housing to limit any movement but without being too tight as to cause components to interfere with each other. Thus, there is a need for housings that can significantly increase the protection of components while also providing for reliable connections and limited interference without requiring additional space.

To address these limitations and problems, implantable medical device described herein include a sealed housing (e.g., a hermetically sealed housing) defining a housing interior. The sealed housing is described herein as a "nest housing" because in addition to providing protection to electronics components within the housing interior (encapsulation), the housing acts as a substrate and an insulator for supporting and/or connecting electronic components within the housing interior. One illustrative embodiment of the present disclosure is directed to a medical device comprising: a first nest portion; a second nest portion mateable with the first nest portion to form a nest housing, where the nest housing comprises an interior surface and an exterior surface; a component cavity defined by the interior surface; an electronics module disposed within a first region of the component cavity, where the electronics module comprises a processor, a pulse generator, a non-transitory machine readable storage medium, or any combination thereof; a power source disposed within a second region of the component cavity; and an electrical interconnect formed on or embedded within the first nest portion, the second nest portion, or a combination thereof, where the electrical interconnect electrically connects the electronics module to the power source and optionally to a feedthrough.

In other embodiments, an implantable neurostimulator is provided for that includes: a nest housing comprising an interior surface and an exterior surface; a component cavity defined by the interior surface; an electronics module disposed within a first region of the component cavity, where the electronics module comprises a processor and a pulse generator; a power source disposed with a second region of the component cavity; an electrical interconnect formed on or embedded within a portion of the nest housing, where the electrical interconnect electrically connects the electronics module to the power source; a cap bonded to the nest housing; and one or more feedthroughs that pass through the cap, where the electronics module is electrically connected to the one or more feedthroughs; and lead assembly including: a lead body including a conductor material; a lead connector that connects the conductor material to the one or more feedthroughs; and one or more electrodes connected to the conductor material. In an alternative to bonding the cap to the nest housing, the cap may be structurally welded or otherwise fixedly attached to a hermetic casing surrounding the nest housing and electrically connected to the electronics module. Other methods of fixing the cap to the nest housing may include metallic (e.g., gold) brazing, diffusion bonding, soldered, laser welding, and the like.

In other embodiments, a medical device is provided for that comprises: a nest housing comprising one or more layers of dielectric material, where the one or more layers of dielectric material form an interior surface and an exterior surface of the nest housing; a component cavity defined by the interior surface; a first electronic component disposed within the component cavity; a second electronic component disposed within the component cavity; an electrical interconnect formed on or embedded within the one or more layers of dielectric material; a first electrical contact disposed between the electrical interconnect and the first electronic component; and a second electrical contact disposed between the electrical interconnect and the second electronic component, where the electrical interconnect electrically connects the first electronic component and the second electronic component via the first electrical contact and the second electrical contact. In some embodiments, electrical contacts are one or more of a spring clip, a pogo pin, a contact pad, or a combination thereof. Electrical contacts may also be a metallic threaded insert that interfaces with a plated through hole disposed on the electronics module in order to make a secure connection. Another exemplary electrical contact may be an edge connector, or an array of pads on the edge of an electronics module for securing a connection. Yet another exemplary electrical contact may include a separate metal component that is overmolded to the nest housing or as a single-piece construction within the nest housing.

Advantageously, these approaches provide a medical device having a nest housing structure that protects the electronic components and ensures reliable electrical connections while meeting routing density and size tolerances.

II. Active Implantable Medical Devices Having Protective Structures with Integrated Electrical Interconnects FIG. 1 shows a medical device 100 (e.g., a neuromodulation device or a neural control interface device) in accordance with some aspects of the present disclosure. In various embodiments, the medical device 100 includes a housing 105, a feedthrough assembly 110, an electronics module 115, a power source 120, an antenna 125, and a casing 130. The casing 130 is a hard outer shell comprised of materials that are biocompatible such as bioceramics or bioglasses for radio frequency transparency, or metals such as titanium. In some instances, the casing 130 is a substantially continuous protective cover encasing the housing 105. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent. In other instances, the casing 130 is modular and can be mated together to form a protective cover encasing the housing 105. In either instance (continuous or modular), the casing 130 is sealed, e.g., hermetically sealed, such that the casing 130 forms an air tight encapsulation around the housing 105 and a component cavity 140 in which the electronics module 115, power source 120, and antenna 125 reside. In some instances, a layer of compliant material is disposed between the casing 130 and the housing 105. The compliant material may be a material selected from polyurethane, polycarbonate, silicone, polyethylene, fluoropolymer, or combinations thereof. In some instances, the casing 130 is attached or bonded to the housing 105 using an attachment structure such as an adhesive layer or a bonding technique such as plasma surface adhesion. Additionally or alternatively with respect to the compliant material, a selectively applied electrically conductive material may be disposed between the casing 130 and the housing 105.

The housing 130 is a support structure comprised of a first nest portion 145 and a second nest portion 150. The first nest portion 145 and the second nest portion 150 are shown in FIG. 1 unmated or in an open configuration in order to illustrate interior features. However, it should be understood that the first nest portion 145 and the second nest portion 150 are mateable and surround the component cavity 140 in which the electronics module 115, power source 120, and antenna 125 reside. The first nest portion 145 and the second nest portion 150 comprise a substrate, one or more components 155, and optionally an encapsulation layer, as described in detail with respect to FIGS. 2-4. The substrate may, for example, be a soft, flexible, or otherwise stretchable substrate of electrically non-conductive material that can conform to the contour of a surface on which the substrate is disposed. Examples of such surfaces include, but are not limited to, the casing 130. Suitable substrates 110 that may be used include, for example, dielectric materials (e.g., an electrical insulator) such as porcelain, glass, and various polymers or polymeric materials. Non-limiting examples of applicable polymers or polymeric materials include, but are not limited to, a polyimide (PI), a polyethylene terephthalate (PET), a silicone, or a polyurethane. Other non-limiting examples of applicable polymers or polymeric materials include plastics (including a thermoplastic, a thermoset plastic, or a biodegradable plastic), elastomers (including a thermoplastic elastomer, a thermoset elastomer, or a biodegradable elastomer), and fabrics (including a natural fabric or a synthetic fabric), such as but not limited to acrylates, acetal polymers, cellulosic polymers, fluoropolymers, nylons, polyacrylonitrile polymers, polyarylates, polybenzimidazole, polybutylene, polycarbonate, polyesters, polyetherimide, polyethylenes, polyketones, polymethylpentene, polyphenylenes, polyphthalamide, polypropylene, polyurethanes, resins, or any combinations of these materials. The substrate can be formed using any suitable process including, for example, casting, molding, stamping, or any other suitable process. Furthermore, the substrate can include other features, for example, holes, protrusions, grooves, indents, non-conducting interconnects, or any other features. In some instances, grooves, which can act as seats for device islands or interconnects, can be formed on the substrate. In some embodiments, the first and second nest portions have a complementary metallization pattern to provide a secure connection between first and second nest portions to form the nest housing. Advantageously, such metallization on the nest could provide an additional benefit for thermal management, in other words, as a radiator routing heat from a primary component and dissipating the heat over a greater surface area.

The components 155 are formed on or embedded within one or more layers of material of the first nest portion 145, the second nest portion 150, or a combination thereof. The components 155 include fit components for improving fitting of electronic components within the component cavity 140 such as spring elements molded into the one or more layers of material or inserted in as a separate element (plastic or metallic) attached to the one or more layers of material. Additionally or alternatively, the components 155 include connection components for improving electrical connection between electronic components within the component cavity 140 such as electrical interconnects embedded into the one or more layers of material or directly printing traces onto the one or more layers of material (MID-style). Additionally or alternatively, the components 150 can include integrated circuit components typically formed on the PCB for conserving space within the component cavity 140 such as the electronic components of the electronics module 115 and/or the antenna 125 formed directly onto the one or more layers of material. Non-limiting examples of components 155 that can be formed on or embedded within one or more layers of material of the first nest portion 145, the second nest portion 150, or a combination thereof include a processing unit, a memory (such as but not limited to a read-only memory, a flash memory, and/or a random-access memory), an input interface, an output interface, a communication module, a passive circuit component, an active circuit component, and the like. In an example, the components 155 comprises an electrical interconnect (i.e., metal traces or wiring layers) that electrically connects the electronics module 115 to the power source 120. In some instances, the components 155 further comprise a microcontroller such as a processing unit of the electronics module 115 and/or other integrated circuit components.

Optionally, an encapsulation layer is formed over at least a portion of the substrate and/or the components 155 such that the encapsulation layer envelopes the portion of the substrate and/or the components 155. In some instances, the encapsulation layer is formed of a material that seals portions (e.g., surfaces) of the components 155 exposed by the substrate. For example, the encapsulation layer may be disposed on the components 155 including the electrical interconnects sealing the components 155 from exposure to the component cavity 140. In such instances, the encapsulation layer can include holes, apertures, or otherwise openings such that a portion(s) of the components 155 are exposed for electrical connection to other components such as the electronics module 115 or the power source 120 within the component cavity 140. The encapsulation layer may be formed from a soft, flexible, and electrically non-conductive material. In some examples, the encapsulation layer is formed from the same material as the substrate. In other examples, a different material can be used to form the encapsulation layer. Suitable materials that can be used in the encapsulation layer include, for example, a polymer or a polymeric material. Non-limiting examples of applicable polymers or polymeric materials include, but are not limited to, a polyimide (PI), a polyethylene terephthalate (PET), a silicone, or a polyurethane. Other non-limiting examples of applicable polymers or polymeric materials include plastics (including a thermoplastic, a thermoset plastic, or a biodegradable plastic), elastomers (including a thermoplastic elastomer, a thermoset elastomer, or a biodegradable elastomer), and fabrics (including a natural fabric or a synthetic fabric), such as but not limited to acrylates, acetal polymers, cellulosic polymers, fluoropolymers, nylons, polyacrylonitrile polymers, polyamide-imide polymers, polyarylates, polybenzimidazole, polybutylene, polycarbonate, polyesters, polyetherimide, polyethylene, polyethylene copolymers and modified polyethylenes, polyketones, poly(methyl methacrylate, polymethylpentene, polyphenylene oxides and polyphenylene sulfides, polyphthalamide, polypropylene, polyurethanes, styrenic resins, sulfone based resins, vinyl-based resins, or any combinations of these materials. In an example, the polymer or polymeric material can be an ultraviolet (UV) curable polymer, such as a UV curable silicone. The encapsulation layer can be formed using any suitable process, for example, casting, molding, stamping, or any other known or hereinafter developed fabrication methods. Furthermore, the encapsulation layer can include a variety of optional features, such as holes, protrusions, grooves, indents, non-conducting interconnects, or any other features.

The first nest portion 145 and the second nest portion 150 have exterior surfaces 160 and interior surfaces 165. The thickness (t) between the exterior surfaces 155 and interior surfaces 160 can be constant through-out the housing 105 or can be variable depending on a number or thickness of layers used to construct various regions of the first nest portion 145 and the second nest portion 150. For example, a region of the first nest portion 145 may have a first thickness as a result of multiple layers of dielectric material used for supporting one or more integrated circuits components; whereas a region of the second nest portion 150 may have a second thickness (less than the first thickness) as a result of less or absence of layers of dielectric material for attachment of fit components. In some instances, the first nest portion 145 has a first perimeter edge surface and the second nest portion 150 has second perimeter edge surface. The first perimeter edge surface and the second perimeter edge surface are disposed between exterior surfaces 160 and interior surfaces 165. Once the first nest portion 145 and the second nest portion 150 are mated to form the housing 105, the first perimeter edge surface and the second perimeter edge surface are in contact and may be bonded, welded, soldered, or otherwise connected fixedly as with a snap fit or other fastener to enclose the component cavity 140.

The feedthrough assembly 110 is attached to a hole in distal end of the housing 105 and is attached so that the housing 105 remains sealed. The feedthrough assembly 110 can include one or more feedthroughs 170 (i.e., electrically conductive elements, pins, wires, tabs, pads, etc.) mounted within and extending through an end of the housing 105 or a cap 175 from an interior of the housing 105 to an exterior of the housing 105. In certain examples, the one or more feedthroughs 170 are made of metal such as copper, silver, gold, or alloys of platinum-iridium. The cap may be formed of bioceramics, bioglasses, or metals such as titanium. In embodiments that include the cap 175, the cap 175 may be mounted or fixed to the housing 105 by fitting the cap 175 into a hole in the housing 105 and metallic (e.g., gold) brazing, diffusion bonding, soldered, or laser welding the cap 175 at an outer perimeter of the cap 175. With the feedthroughs 170 in sealing engagement with housing 105, interior ends of the feedthroughs 170 project from the interior surfaces 165 of the housing 105 or cap 175 into the component cavity 140 of the housing 105 and may be terminated with a connection component or contacts (e.g., connection components or contacts such as electrical interconnects and/or pogo pins, cradles, or other similar connectors embedded into the layers of the first nest portion 145 and the second nest portion 150). In certain embodiments, the termination pad generally lies perpendicular to the longitudinal axis extending through the feedthroughs 170. Exterior ends of the feedthroughs 170 project from the exterior surfaces 160 of the housing 105 or cap 175 to the exterior of the housing 105. Each of the exterior ends extends for connection to a corresponding conductor of a lead. Each of the interior ends extends for connection via the connection component or contacts to the electronics module 115 also located within the component cavity 140 of housing 105.

The electronics module 115 is electrically connected to the interior ends of the one or more feedthroughs 170 such that the electronics module 115 is able to apply or record a signal or electrical current to or from each of the leads connected to the exterior ends of the feedthroughs 170. In some embodiments, the electronics module 115 is connected to the interior ends of the one or more feedthroughs 170 via indirect connection such as electrical interconnects and/or pogo pins, cradles, or other similar connectors embedded into the layers of the first nest portion 145 and the second nest portion 150. The electronics module 115 includes any discrete and/or integrated electronic circuit components that implement analog and/or digital circuits capable of producing the functions attributed to the neuromodulation devices and neural control interface devices described herein. The electronic circuits components are assembled to form the electronics module 115 using various combinations of solder reflow, wire-bonding, flip-chip bonding, etc.

In various embodiments, the electronics module 115 may include electronic circuit components such as a pulse generator that generates a signal or electrical current and one or more processors that determine or sense electrical activity via electrodes and/or deliver electrical stimulation via electrodes. Additionally, electronics module 115 may also include non-transitory machine readable storage medium having instructions stored thereon that when executed by the processor cause the processor to perform one or more operations such as generation of a signal or electric current. Electronics module 115 may also include sensors that sense physiological conditions of a patient, such as an accelerometer and/or a pressure sensor. In certain embodiments, the electronics module 115 is a printed circuit board with an interposer in combination with discrete and/or integrated electronic circuit components such as application specific integrated circuits (ASICs) assembled using either 2.5 or 3D integration to achieve miniaturization. In other embodiments, the electronics module 115 is a combination of integrated circuit components with an interposer in combination with discrete and/or integrated electronic circuit components such as ASICs assembled using either 2.5 or 3D integration to achieve miniaturization and integrated into the layers of the first nest portion 145 and the second nest portion 150.

The power source 120 is within the housing 105 and electrically connected to the electronics module 115 to power and operate the components of the electronics module 115. In some embodiments, the power source 120 is connected to the electronics module 115 via indirect connection such as electrical interconnects and/or pogo pins, cradles, or other similar connectors embedded into the layers of the first nest portion 145 and the second nest portion 150. The power source 120 may be any type of device that is of implant grade and configured to hold a charge to power and operate the components of the electronics module 115. In certain embodiments, the power source is a non-rechargeable battery needing replacement every few years (depending on stimulation parameters) or a rechargeable battery that is replenished via an external inductive charging system.

The antenna 125 is connected (e.g., electrically connected) to the electronics module 115 for wireless communication with external devices via radiofrequency (RF) telemetry or the like. In some embodiments, the antenna 125 is connected to the electronics module 115 via indirect connection such as electrical interconnects and/or pogo pins, cradles, or other similar connectors embedded into the layers of the first nest portion 145 and the second nest portion 150. The wireless communication implemented via the antenna 125 may include receiving information or signals such as power on/off signals, configuration packages to update software, software setting data to configure software, physiological data such a blood pressure from implantable or external sensors, etc., and relay important information or signals (e.g., electrocardiogram and blood pressure) from sensors or the one or more processors on the electronics module 115 or the electrodes to external equipment to be analyzed or to guide treatment.

Figure 2:
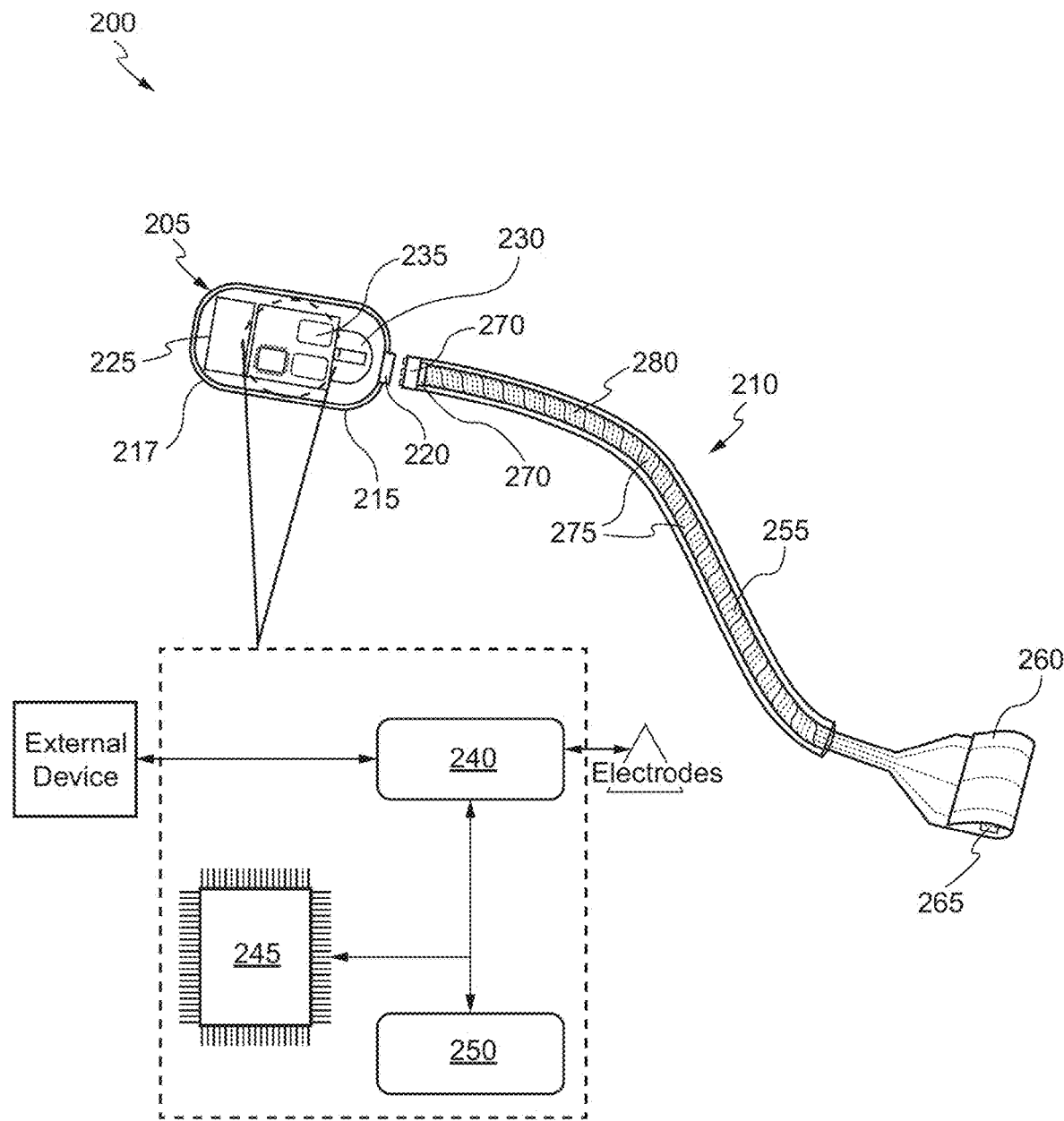
FIG. 2 shows a medical device system in accordance with various embodiments.

FIG. 2 shows a neuromodulation or neural control interface system 200 in accordance with some aspects of the present invention. In various embodiments, the neuromodulation or neural control interface system 200 includes an implantable device 205 (e.g., the medical device 100 discussed with respect to FIG. 1) and a lead assembly 210. The implantable device 205 may include a casing 215, a housing 217, a feedthrough assembly 220, a power source 225, an antenna 230, and an electronics module 235 (e.g., a computing system). The casing 215 may be comprised of materials that are biocompatible such as bioceramics or bioglasses for radio frequency transparency, or metals such as titanium. In addition to titanium, suitable metals and alloys may include gold, platinum, silver, iridium, tantalum, tungsten, stainless steel, cobalt-chrome alloy, and nickel-titanium alloy (nitinol). The housing 217 is a support structure comprised of a first nest portion and a second nest portion. The first nest portion and the second nest portion comprise a substrate, one or more components, and optionally an encapsulation layer. In accordance with some aspects of the present invention, the size and shape of the casing 215 and housing 217 may be selected such that the implantable device 205 can be implanted within a patient. In the example shown in FIG. 2, the feedthrough assembly 220 is attached to a hole in a surface of the casing 215 such that the casing 215 is hermetically sealed. The feedthrough assembly 220 may include one or more feedthroughs (i.e., electrically conductive elements, pins, wires, tabs, pads, etc.) mounted within and extending through the surface of the casing 215 or a cap from an interior to an exterior of the casing 215. The power source 225 may be within the housing 217 and connected (e.g., electrically connected) to the electronics module 235 to power and operate the components of the electronics module 235. The antenna 230 may be connected (e.g., electrically connected) to the electronics module 235 for wireless communication with external devices via, for example, radiofrequency (RF) telemetry.

In some embodiments, the electronics module 235 may be connected (e.g., electrically connected) to interior ends of the feedthrough assembly 220 such that the electronics module 235 is able to apply a signal or electrical current to conductive traces of the lead assembly 210 connected to exterior ends of the feedthrough assembly 220. An intermediate barrel-style connector (not shown) may be positioned between the lead assembly 210 and the feedthrough assembly 220. The electronics module 235 may include discrete and/or integrated electronic circuit components that implement analog and/or digital circuits capable of producing the functions attributed to the neuromodulation devices or systems such as applying or delivering neural stimulation to a patient. In various embodiments, the electronics module 235 may include software and/or electronic circuit components such as a pulse generator 240 that generates a signal to deliver a voltage, current, optical, or ultrasonic stimulation to a nerve or artery/nerve plexus via electrodes, a controller 245 that determines or senses electrical activity and physiological responses via the electrodes and sensors, controls stimulation parameters of the pulse generator 240 (e.g., control stimulation parameters based on feedback from the physiological responses), and/or causes delivery of the stimulation via the pulse generator 240 and electrodes, and a memory 250 with program instructions operable on by the pulse generator 240 and the controller 245 to perform one or more processes for applying or delivering neural stimulation.

In various embodiments, the lead assembly 210 is a monolithic structure that includes a cable or lead body 255. In some embodiments, the lead assembly 210 further includes one or more electrode assemblies 260 having one or more electrodes 265, and optionally one or more sensors. In some embodiments, the lead assembly 210 further includes a connector 270. In certain embodiments, the connector 270 is bonding material that bonds conductor material of the cable 255 to the electronics module 235 of the implantable device 205 via the feedthrough assembly 220. The bonding material may be a conductive epoxy or a metallic solder or weld such as platinum. In other embodiments, the connector 270 is conductive wire, conductive traces, or bond pads (e.g., a wire, trace, or bond pads formed of a conductive material such as copper, silver, or gold) formed on a substrate and bonds a conductor of the cable 255 to the electronics module 235 of the implantable device 205. In alternative embodiments, the implantable device 205 and the cable 255 are designed to connect with one another via a mechanical connector 270 such as a pin and sleeve connector, snap and lock connector, flexible printed circuit connectors, or other means known to those of ordinary skill in the art.

The cable 255 may include one or more conductive traces 275 formed on a supporting structure 280. The one or more conductive traces 275 allow for electrical coupling of the electronics module 235 to the electrodes 265 and/or sensors of the electrode assemblies 260. The supporting structure 280 may be formed with a dielectric material such as a polymer having suitable dielectric, flexibility and biocompatibility characteristics. Polyurethane, polycarbonate, silicone, polyethylene, fluoropolymer and/or other medical polymers, copolymers and combinations or blends may be used. The conductive material for the traces 275 may be any suitable conductor such as stainless steel, silver, gold, alloys of platinum-iridium, or other biocompatible conductive materials, which may have separate coatings or sheathing for anticorrosive, insulative and/or protective reasons.

The electrode assemblies 260 may include the electrodes 265 and/or sensors fabricated using various shapes and patterns to create certain types of electrode assemblies (e.g., book electrodes, split cuff electrodes, spiral cuff electrodes, epidural electrodes, helical electrodes, probe electrodes, linear electrodes, neural probe, paddle electrodes, intraneural electrodes, etc.). In various embodiments, the electrode assemblies 260 include a base material that provides support for microelectronic structures including the electrodes 265, a wiring layer, optional contacts, etc. In some embodiments, the base material is the supporting structure 280. The wiring layer may be embedded within or located on a surface of the supporting structure 280. The wiring layer may be used to electrically connect the electrodes 265 with the one or more conductive traces 275 directly or indirectly via a lead conductor. The term "directly", as used herein, may be defined as being without something in between. The term "indirectly", as used herein, may be defined as having something in between. In some embodiments, the electrodes 265 may make electrical contact with the wiring layer by using the contacts

III. Protective Structures with Integrated Electrical Interconnects

Figure 3A:
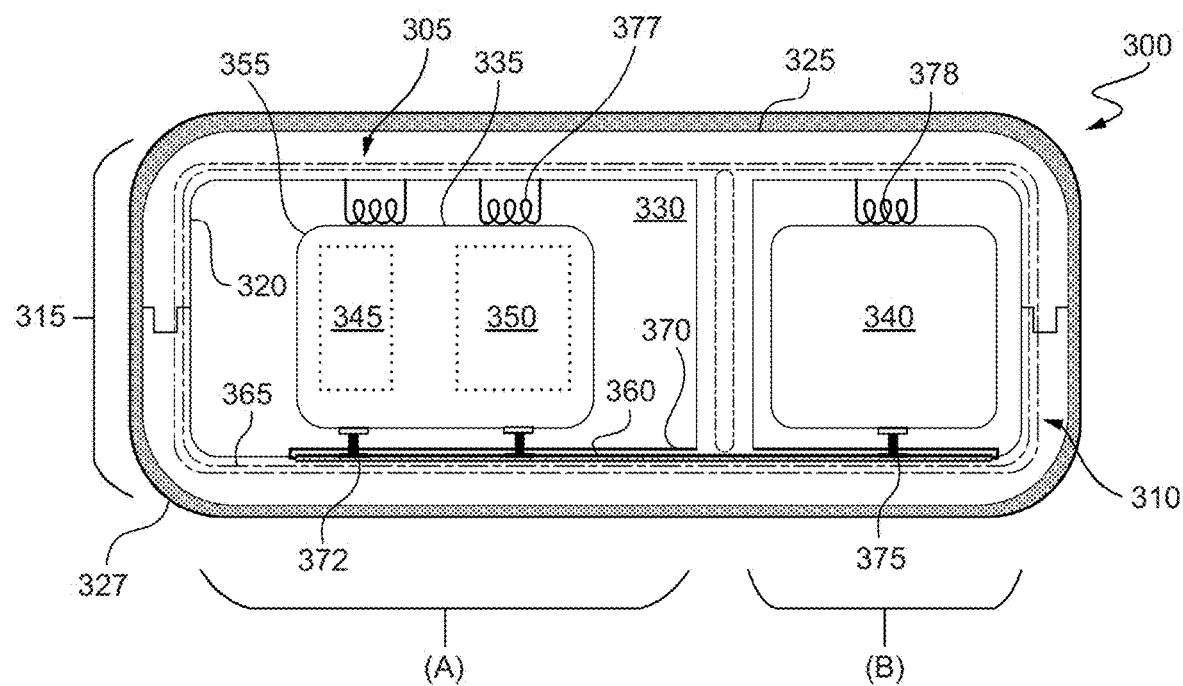
FIG. 3A shows a cross-sectional view of medical device having a nest housing in accordance with various embodiments.

FIG. 3A shows a first cross sectional view of a medical device 300 (e.g., the medical device 100 discussed with respect to FIG. 1). The medical device 300 comprises a first nest portion 305 and a second nest portion 310 mateable with the first nest portion 305 to form a nest housing 315. The nest housing 315 comprises an interior surface 320 and an exterior surface 325. In some instances, the medical device 300 further comprises a casing 327 that is directly or indirectly in contact with at least a portion of the exterior surface 325 of the housing 315. In certain instances, a layer of compliant material or a layer of adhesive material is disposed between the exterior surface 325 of the housing 315 and the casing 327. A component cavity 330 is defined by the interior surface 320. In some instances, an electronics module 335 is disposed within a first region (A) of the component cavity 330 and a power source 340 is disposed within a second region (B) of the component cavity 330. In certain instances, the electronics module 335 comprises a processor 345 and a non-transitory machine readable storage medium 350 having instructions stored thereon that when executed by the processor 345 cause the processor 345 to perform one or more operations. In some instances, the electronics module 335 is a PCBA. In certain instances, the electronics module 335 is formed on a PCB 355.

The medical device 300 further comprises an electrical interconnect 360 formed on or embedded within the first nest portion 305, the second nest portion 310, or a combination thereof. In some instances, the electrical interconnect 360 electrically connects the electronics module 335 to the power source 340. The electrical interconnect 360 are formed on or embedded within in the first nest portion 305, the second nest portion 310, or a combination thereof via wire conduits (e.g., wiring or metallization layers) or directly printing traces onto the first nest portion 305, the second nest portion 310, or a combination thereof (MID-style). In some instances, the electrical interconnect 360 is a wire, a drawn filled tube, a helical coiled conductor, a microwire, a conductive metal trace, or a printed circuit. The first nest portion 305, the second nest portion 310, or a combination thereof comprise one or more layers of dielectric material 365 (i.e., a substrate) and the electrical interconnect 360 is formed on (see FIG. 3A) or embedded within (see FIG. 3B) the one or more layers of dielectric material 365. In some instances, the dielectric material is a polyimide, a liquid crystal polymer (LCP), parylene, polyether ether ketone (PEEK), or a combination thereof. In some instances, the electrical interconnect 360 comprises a conductive material and the conductive material is copper (Cu), gold (Au), silver (Ag), gold/chromium (Au/Cr), platinum (Pt), platinum/iridium (Pt/Ir), titanium (Ti), gold/titanium (Au/Ti), or any alloy thereof. The electrical interconnect 360 may include traces formed on or embedded within the nest housing or portions thereof. Optionally, an encapsulation layer 370 is formed over at least a portion of the electrical interconnect 360 and/or a portion of the one or more layers of dielectric materials 365.

The medical device 300 further comprises one or more connection components, for example, a first electrical contact 372 disposed between the electrical interconnect 360 and the electronics module 335 and a second electrical contact 375 disposed between the electrical interconnect 360 and the power source 340. The connection components may be formed on or embedded within the first nest portion 305, the second nest portion 310, or a combination thereof (e.g., the one or more layers of dielectric material 165). This allows for the nest housing 315 to provide a force on the first electrical contact 372 and the second electrical contact 375 to maintain electrical connection between the electronics module 335 and the power source 340 via the first electrical contact 372, the second electrical contact 375, and the electrical interconnect 360. The connection components may be used to electrically connect components with the electrical interconnect 360, or may be used as a mechanical restraint for components within the component cavity 330. In some instances, the connection components are bonding material that bonds the conductive material of the electrical interconnect 360 to components such as the electronics module 335 and/or the power source 340. The bonding material may be a conductive epoxy or a metallic solder or weld such as platinum. In other instances, the connection components are conductive wire, conductive traces, or bond pads (e.g., a wire, trace, or bond pads formed of a conductive material such as copper, silver, or gold) formed on a substrate and bonds the conductive material of the electrical interconnect 360 to the components such as the electronics module 335 and/or the power source 340. In other instances, the connection components are a mechanical connector such as a spring clip, a pogo pin, cradles, a sleeve connector, snap and lock connector, flexible printed circuit connectors, or other means known to those of ordinary skill in the art. As should be understood, any number of connection components may be used within the medical device 300, and the connection components can be the same type of electrical contacts or different types of connection components or combinations thereof. As also should be understood, a first electrical contact may be one or more electrical contacts (as in a set) or a plurality of electrical contacts. Similarly, a second electrical contact and a third electrical contact may each be one or more electrical contacts (as in a set) or a plurality of electrical contacts.

The medical device 300 further comprises one or more fit components, for example, a first fit component 377 disposed between the first nest portion 305, the second nest portion 310, or a combination thereof and the electronics module 335 and a second fit component 378 disposed between the first nest portion 305, the second nest portion 310, or a combination thereof and the power source 340. The one or more fit components may be formed on or embedded within the first nest portion 305, the second nest portion 310, or a combination thereof (e.g., the one or more layers of dielectric material 165). This allows for the one or more fit components to further provide a force on the first electrical contact 372 and the second electrical contact 375 to maintain electrical connection between the electronics module 335 and the power source 340 via the first electrical contact 372, the second electrical contact 375, and the electrical interconnect 360. In some instances, the one or more fit components are spring elements molded into structure or inserted in as a separate element (plastic or metallic). In other embodiments, the one or more fit components are coil springs, leaf springs, or any other structure that will provide preload when deformed during device assembly (such as an angled tab with a side pull). While the one or more fit components are shown formed on or embedded within the first and/or second nest portions, yet other embodiments, the one or more fit components may be disposed fixedly or otherwise installed directly to the electronics module 335 and/or the power source 340 for contact or impingement onto the first and/or second nest portions. In addition to securing connections mechanically, the fit components may provide and maintain electrical connection between the electronics module and the power source via the electrical contact(s) as well as providing thermal management within the components cavity 330. While not shown, in some embodiments, at least one of the one or more fit components and/or the one or more electrical contacts may be connected or fixed to the casing 327. The casing 327 may therefore provide another channel for the device 300 (similarly also for device 100, or device 400 as described below) by connecting, via soldering, welding, or otherwise electrically bonding, to the appropriate circuit of the electronics module 335.

Figure 3B:
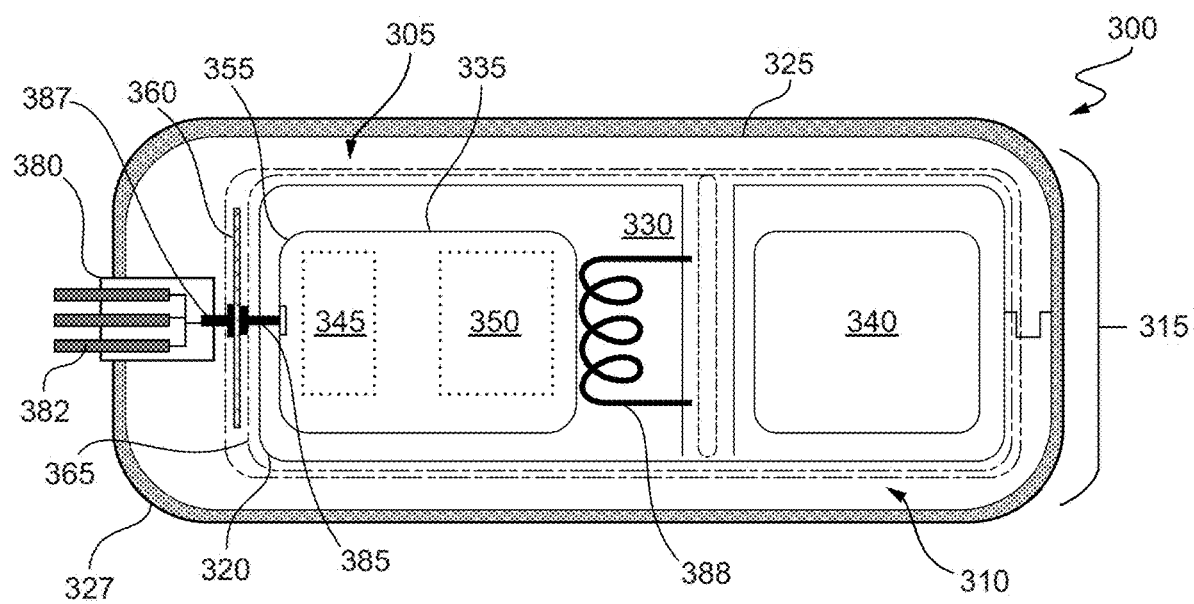
FIG. 3B shows an alternative cross-sectional view of medical device having a nest housing in accordance with various embodiments.

FIG. 3B shows a second cross sectional view of a medical device 300 (e.g., the medical device 100 discussed with respect to FIG. 1; same configuration as described with respect to FIG. 3A or a different configuration or arrangement of components). As described herein, the medical device 300 comprises a first nest portion 305 and a second nest portion 310 mateable with the first nest portion 305 to form a nest housing 315. The medical device 300 further comprises a cap 380 bonded to the nest housing 315, and one or more feedthroughs 382 that pass through the cap 380. As shown in FIG. 3B, an electrical interconnect 360 electrically connects the electronics module 335 to the power source 340 and a feedthrough 382. The electronics module 335 is electrically connected to the one or more feedthroughs 382. In some instances, the electronics module 335 is electrically connected to the one or more feedthroughs 382 via one or more connection components (e.g., a third and fourth electrical contact 385; 387) and the electrical interconnect 360, as described herein. Moreover, in certain instances, one or more fit components (e.g., a third fit component 388) are disposed between the first nest portion 305, the second nest portion 310, or a combination thereof and the electronics module 335 to apply a force on the third and fourth electrical contact 385; 387 to maintain electrical connection between the electronics module 335 and the one or more feedthroughs 382 via the third and fourth electrical contact 385; 387, and the electrical interconnect 360.

Figure 3C:
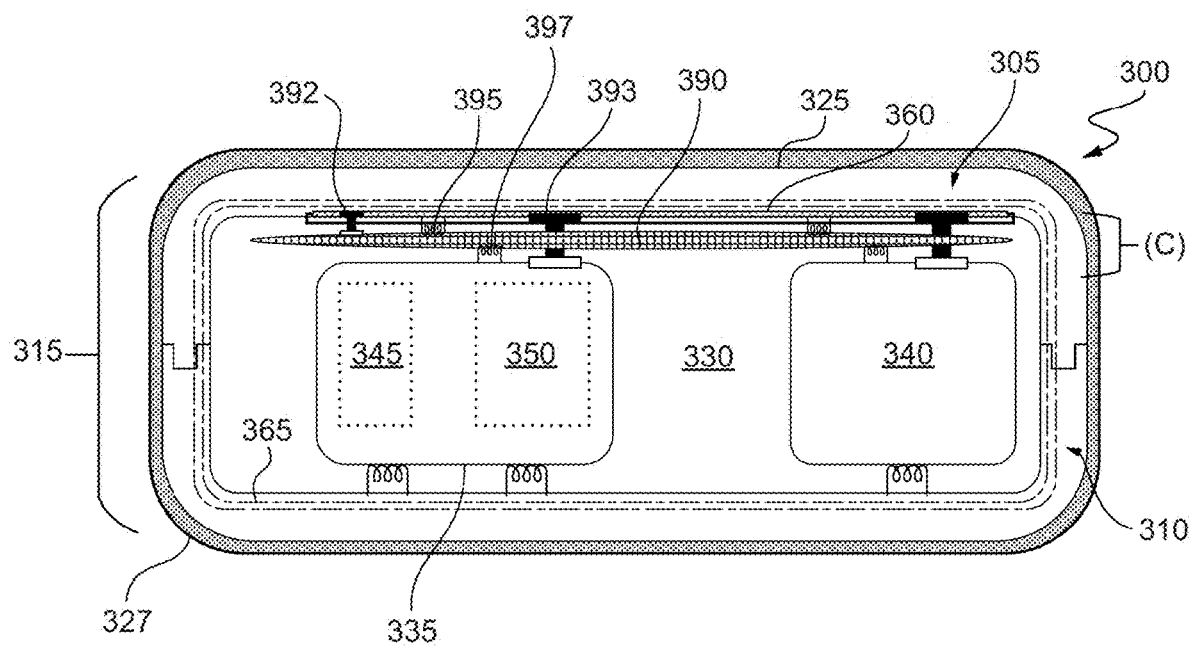
FIG. 3C shows an alternative cross-sectional view of medical device having a nest housing in accordance with various embodiments.

FIG. 3C shows a third cross sectional view of a medical device 300 (e.g., the medical device 100 discussed with respect to FIG. 1; same configuration as described with respect to FIG. 3A/3B or a different configuration or arrangement of components). As described herein, the medical device 300 comprises a first nest portion 305 and a second nest portion 310 mateable with the first nest portion 305 to form a nest housing 315. The medical device 300 further comprises an antenna 390. In some instances, the antenna 390 is a wireless charging antenna or a wireless communication antenna. In some instances, multiple antennas are disposed within the component cavity 330, e.g., a wireless charging antenna and a wireless communication antenna. The antenna 390 may be disposed within a third region (C) of the component cavity 330. The electronics module 335 and/or the power source 340 are electrically connected to the antenna 390. In some instances, the electronics module 335 and/or the power source 340 are electrically connected to the antenna 390 via one or more connection components (e.g., a fifth and sixth electrical contact 392; 393) and the electrical interconnect 360, as described herein. Moreover, in certain instances, one or more fit components (e.g., a fourth and fifth fit components 395; 397) are disposed between the first nest portion 305, the second nest portion 310, or a combination thereof, the electronics module 335 and/or the power source 340, and the antenna 390 to apply a force on the fifth and sixth electrical contact 392; 393 to maintain electrical connection between the electronics module 335 and/or the power source 340 and the antenna 390 via the fifth and sixth electrical contact 392; 393, and the electrical interconnect 360.

Figure 3D:
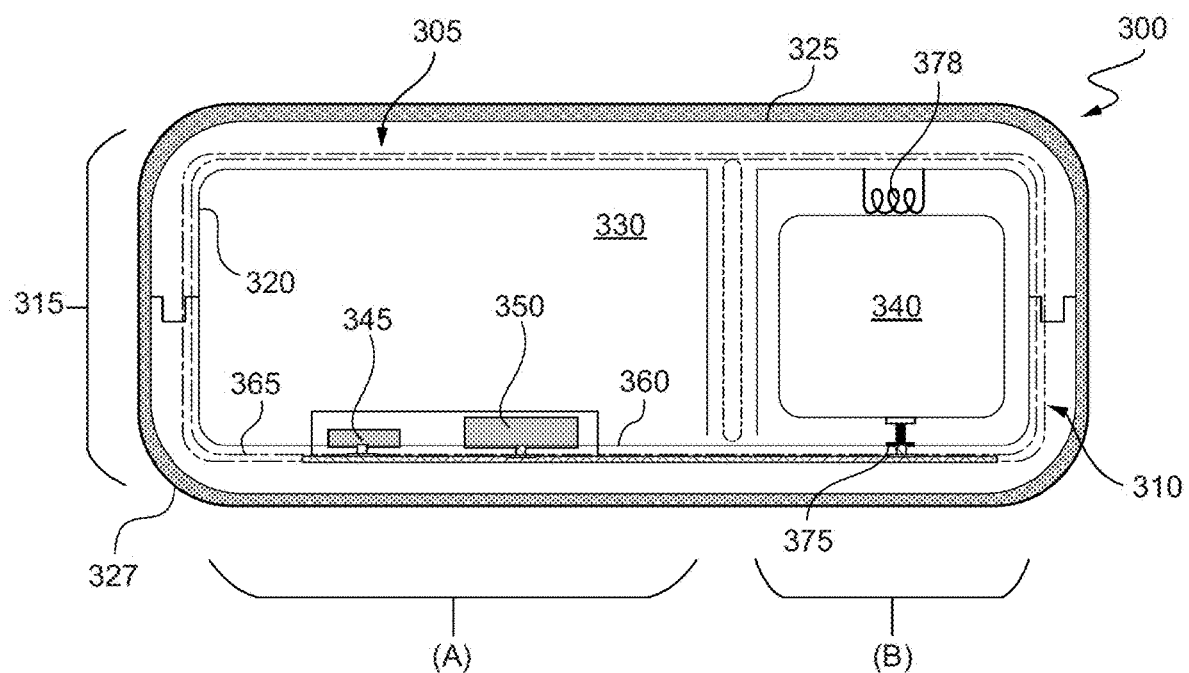
FIG. 3D shows an alternative cross-sectional view of medical device having a nest housing in accordance with various embodiments.

FIG. 3D shows a fourth cross sectional view of a medical device 300 (e.g., the medical device 100 discussed with respect to FIG. 1; a different configuration or arrangement of components). As described herein, the medical device 300 comprises a first nest portion 305 and a second nest portion 310 mateable with the first nest portion 305 to form a nest housing 315. The nest housing 315 comprises an interior surface 320 and an exterior surface 325. In some instances, integrated circuit components such as the processor 345 and/or the non-transitory machine readable storage medium 350 of the electronics module 335 are formed on or embedded within the first nest portion 305, the second nest portion 310, or a combination thereof (as compared to the typical PCB). As illustrated, the electrical interconnect 360 may be formed on or embedded within the one or more layers of dielectric material 365, and the integrated circuit components may be formed on or embedded within the one or more layers of dielectric material 365 in electrical contact with the electrical interconnect 360 such that the integrated circuit components may be connected to one another and other components within the component cavity 330 such as the power source 340. The integrated circuit components may be placed in direct electrical connection with the electrical interconnect 360 or indirectly using via contacts.

Figure 4A:
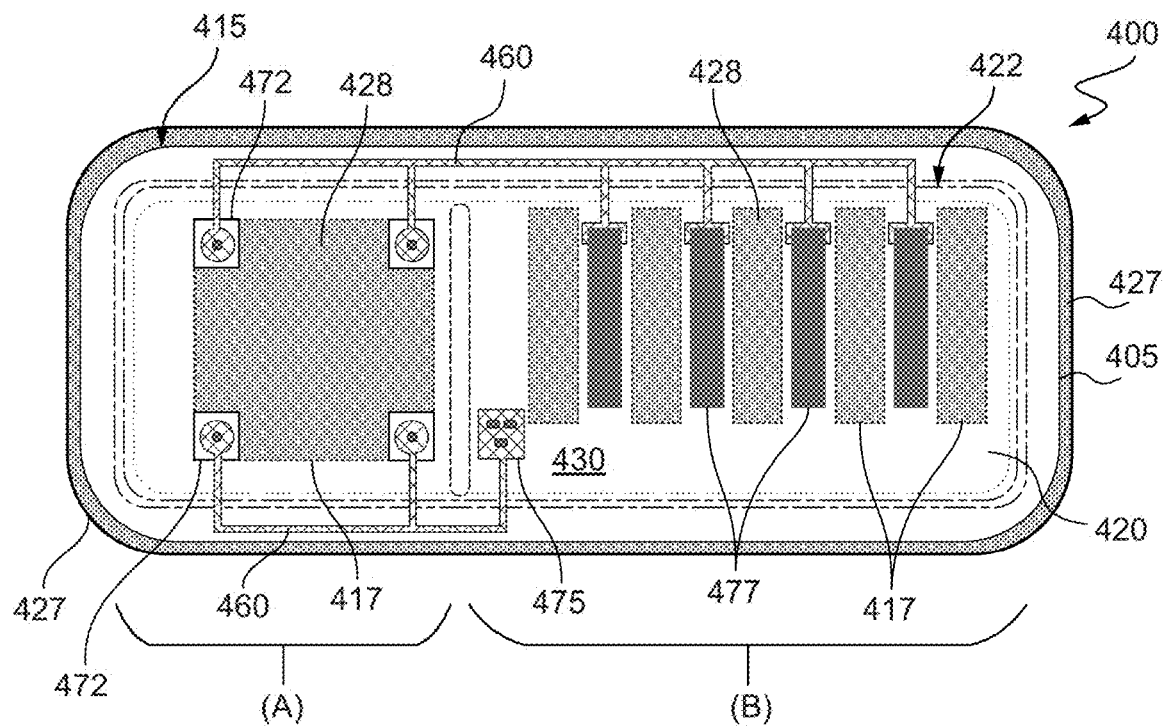
FIG. 4A shows a top view of an alternative medical device having a nest housing in accordance with various embodiments.

FIG. 4A shows a top view of a first nest portion 405 of a medical device 400 (e.g., the medical device 100 discussed with respect to FIG. 1) in an unmated or in an open configuration. The medical device 400 comprises a first nest portion 405 and a second nest portion 410 (not shown) mateable with the first nest portion 405 to form a nest housing 415. The nest housing 415 comprises an interior surface 420, evident in this open configuration view, and an exterior surface 425 (not shown) opposite the interior surface 420. In some instances, the medical device 400 further comprises a casing 427 that is directly or indirectly in contact with at least a portion of the exterior surface 425 of the housing 415. In the view illustrated in FIG. 4A, portions of an interior surface 428 of casing 427, which underlies nest portion 405, are revealed due to openings 417 within the first nest portion 405. Nest portion 405 provides structure as well as electrical connections within medical device 400. Openings 417 provide added space for clearance of components and/or the addition of desiccant into the component cavity 430. Openings 417 may also allow for heat to escape to casing 427. In another aspect, the openings 417 can save on material usage (and cost) as well as potentially providing moldability of the nest housing 415 if needed and can save on mass, which may be important in some implantables. In certain instances, a layer of compliant material or a layer of adhesive material is disposed between the exterior surface 425 of the housing 415 and the casing 427. A component cavity 430 is defined by the interior surface 420, and interior surface 420 may include an angled or curved portion 422 as indicated by dashed lines.

Figure 4B:
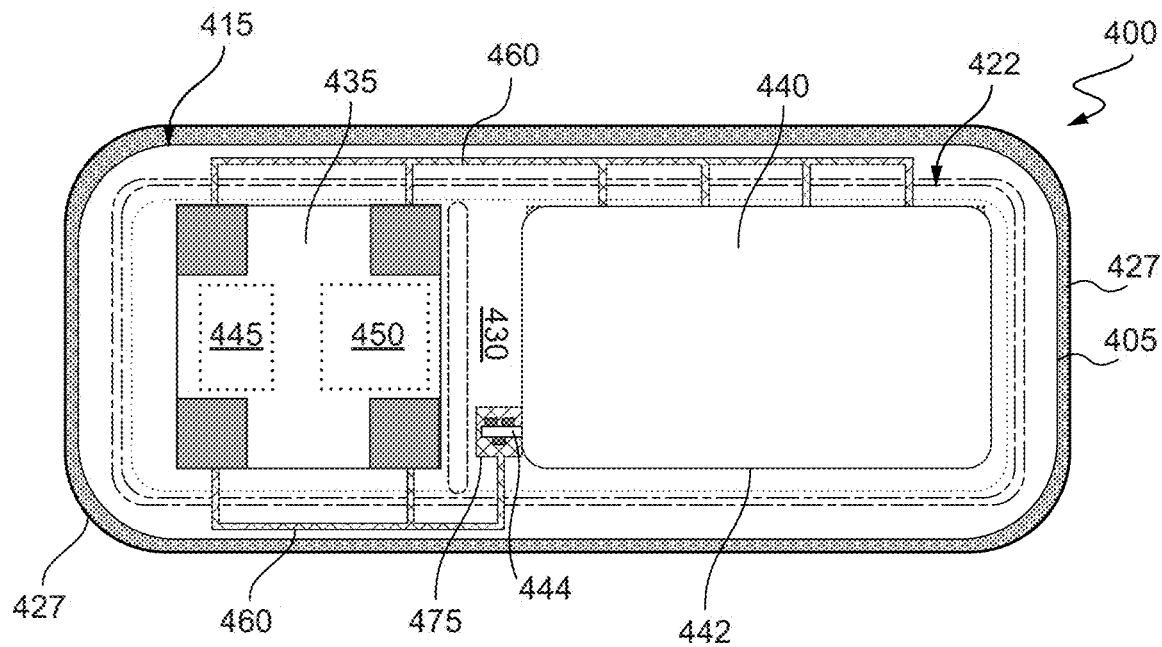
FIG. 4B shows the view of FIG. 4A further including an electronics module and a power source.

The medical device 400 further comprises an electrical interconnect 460 formed on or embedded within the first nest portion 405, and may also be embedded in the second nest portion 410 (not shown), or a combination thereof. The electrical interconnect 460 may be formed on or embedded within the angled or curved portion 422. In some instances, the electrical interconnect 460 electrically connects an electronics module 435 to a power source 440, as shown in FIG. 4B. The electrical interconnect 460 are formed on or embedded within in the first nest portion 405, the second nest portion 410, or a combination thereof via wire conduits (e.g., wiring or metallization layers) or directly printing traces onto the first nest portion 405, the second nest portion 410, or a combination thereof (MID-style). In some instances, the electrical interconnect 460 is a wire, a drawn filled tube, a helical coiled conductor, a microwire, a conductive metal trace, or a printed circuit. The first nest portion 405, the second nest portion 410, or a combination thereof comprise one or more layers of dielectric material (i.e., a substrate) and the electrical interconnect 460 is formed on or embedded within the one or more layers of dielectric material (similarly as shown for dielectric material 365 in FIG. 3A, for example). In some instances, the dielectric material is a polyimide, a liquid crystal polymer (LCP), parylene, polyether ether ketone (PEEK), or a combination thereof. In some instances, the electrical interconnect 460 may include conductive traces comprising a conductive material and the conductive material is copper (Cu), gold (Au), silver (Ag), gold/chromium (Au/Cr), platinum (Pt), platinum/iridium (Pt/Ir), titanium (Ti), gold/titanium (Au/Ti), or any alloy thereof. Optionally, an encapsulation layer (not shown) is formed over at least a portion of the electrical interconnect 460 and/or a portion of the one or more layers of dielectric materials on interior surface 420.

The medical device 400 further comprises one or more connection components, for example, a first electrical contact 472 disposed between the electrical interconnect 460 and the electronics module 435 and a second electrical contact 475 disposed between the electrical interconnect 460 and the power source 440. The connection components may be formed on or embedded within the first nest portion 405, the second nest portion 410, or a combination thereof (e.g., the one or more layers of dielectric material 165 of FIG. 1). This allows for the nest housing 415 to provide a force on the first electrical contact 472 and the second electrical contact 475 to maintain electrical connection between the electronics module 435 and the power source 440 via the first electrical contact 472, the second electrical contact 475, and the electrical interconnect 460. Connection components may be used to electrically connect components with the electrical interconnect 460, or may be used as a mechanical restraint for components within the component cavity 430, or both. In some instances, the connection components are bonding material as described above that bonds the conductive material of the electrical interconnect 460 to components such as the electronics module 435 and/or the power source 440. The bonding material may be a conductive epoxy or a metallic solder or weld such as platinum. In other instances, the connection components are conductive wire, conductive traces, or bond pads (e.g., a wire, trace, or bond pads formed of a conductive material such as copper, silver, or gold) formed on a substrate and bonds the conductive material of the electrical interconnect 460 to the components such as the electronics module 435 and/or the power source 440. In other instances, the connection components may include one or more mechanical connector such as a spring clip, a pogo pin, cradles, a sleeve connector, snap and lock connector, flexible printed circuit connectors, or other means known to those of ordinary skill in the art. As shown in FIG. 4A, first electrical contact 472 are pogo pins for connecting the electrical interconnect 460 to the electronics module 435. The pogo pins of the first electrical contact 472 are embedded into nest portion 405. Also shown in FIG. 4A is second electrical contact 475, which includes a connector array for receiving a battery pin, where the power source 440 includes the battery pin. Second electrical contact 475 may include shaped conductive sheet metal strips embedded directly into the nest portion 405. The connector array of second electrical contact 475 may be spring loaded to retain the battery pin mechanically to ensure a solid electrical connection. Also shown in FIG. 4A are third electrical contacts 477, which may be leaf springs, to provide electrical contact and mechanical security for the body of power source 440 within components cavity 430. The electrical interconnect 460 may include traces directly embedded into nest portion 405. The surrounding area of contacts 472, 475, and 477 may be metallized to form a trace for connecting with electrical interconnect 460. The trace connecting to third electrical contacts 477 is embedded on angled or curved surface 422. As should be understood, any number of connection components may be used within the medical device 400, and the connection components can be the same type of electrical contacts or different types of connection components or combinations thereof. Connection components may also be press fit or overmolded into the first nest portion, the second nest portion, or a combination thereof.

FIG. 4B shows the open configuration view as in FIG. 4A and further including electronics module 435 and power source 440 disposed within components cavity 430. In some instances, an electronics module 435 is disposed within a first region (A) of the component cavity 430 and a power source 440 is disposed within a second region (B) of the component cavity 430. In certain instances, the electronics module 435 comprises a processor 445 and a non-transitory machine readable storage medium 450 having instructions stored thereon that when executed by the processor 445 cause the processor 445 to perform one or more operations. In some instances, the electronics module 435 is a PCBA. While electronics module 435 is shown as a separate component, in some embodiments traces and electrical interconnects may be integrally formed onto or embedded within the nest portion 405 and/or the mateable nest portion 410 so that a separate electronics module, such as a PCB, is not needed and is rather build into the nest housing 415. Electronics module 435, as in FIG. 4B, is fixedly connected to connections 472 (of FIG. 4A), thus securing the electronics module 435. Likewise, power source 440 is fixedly connected with the power source body 442 secured by connections 477 (of FIG. 4A) and battery pin 444 fixed into connection 475 (of FIG. 4A).

Figure 4C:
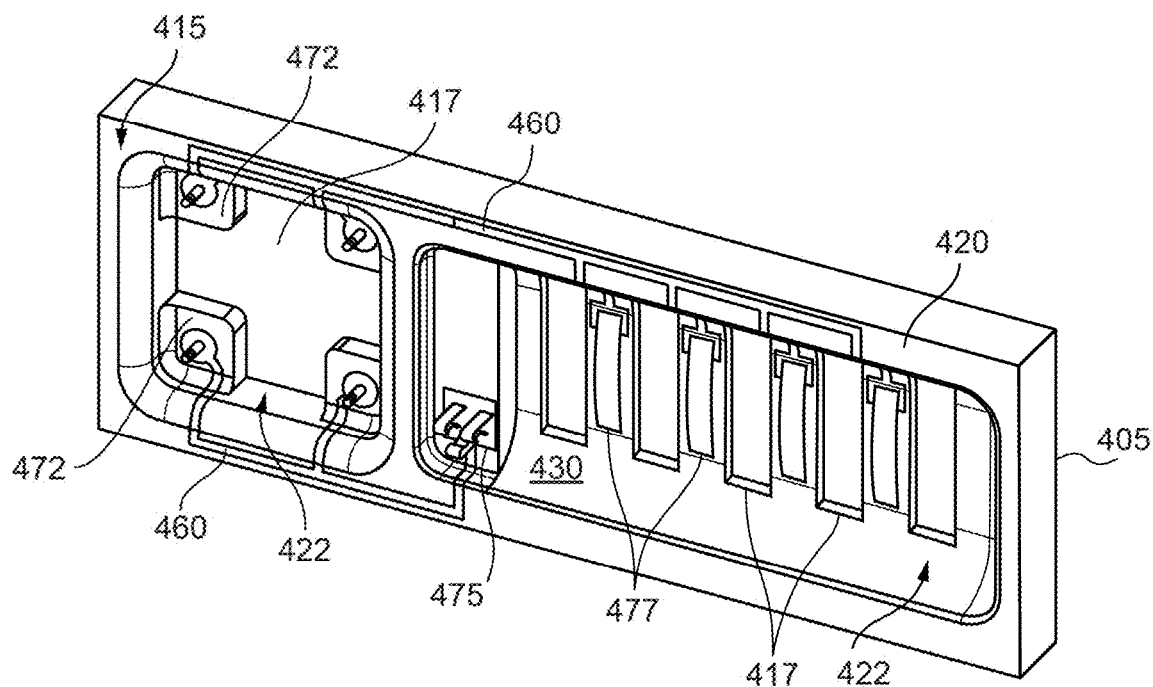
FIG. 4C shows a perspective view of a nest portion of FIG. 4A.
Figure 4D:
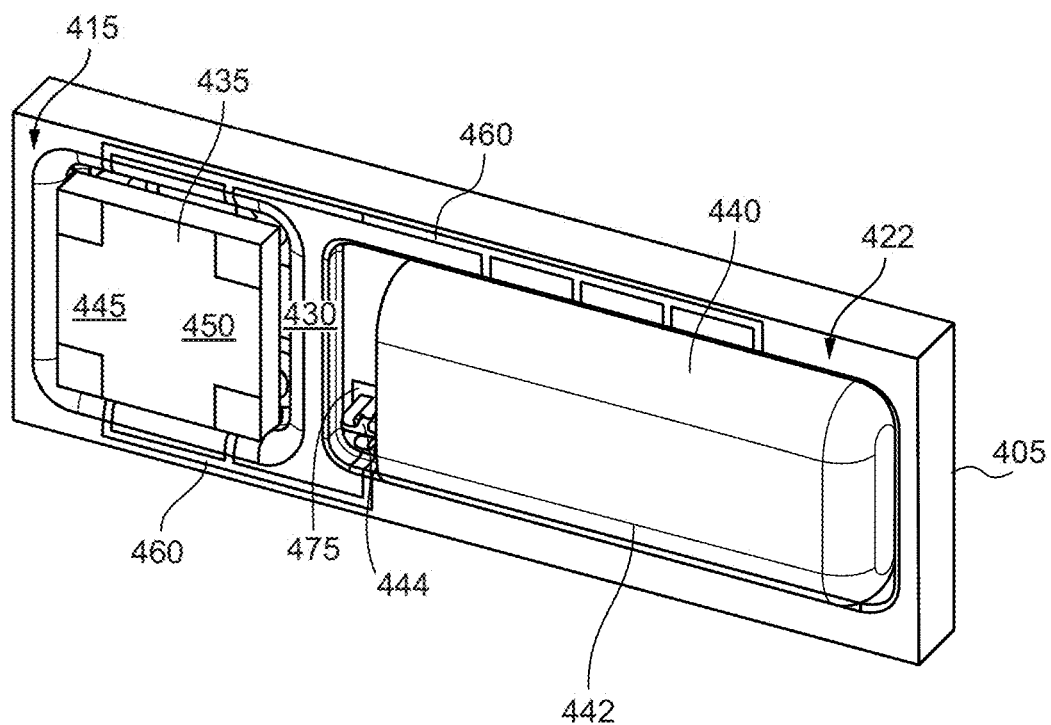
FIG. 4D shows a perspective view of FIG. 4B.

FIG. 4C shows a perspective view of nest portion 405 of FIG. 4A, shown without casing 427. Nest portion 405 of nest housing 415 is shown unmated. Electrical connections 472, 475, and 477 as shown may protrude toward the interior of the component cavity 430. At least some of the electrical connections provide for a more secure fit for subsequently installed components in component cavity 430, for example the electronics module 435 and the power source 440 as shown in FIG. 4D. Nest portion 405 includes openings 417. Electrical interconnect 460 connects electrical connections 472, 475, and 477. Curved portion(s) 422 provide contour and depth as needed for the components cavity 430. As shown in FIG. 4D, the electronics module 435 and the power source 440 are disposed within components cavity 430. Electronics module 435 is electrically connected via electrical connections 472 (as shown in FIG. 4C), and power source body 442 of power source 440 is electrically connected via electrical connections 477 (as shown in FIG. 4C) and additionally via electrical connection 475 receiving battery pin 444.

Figure 4E:
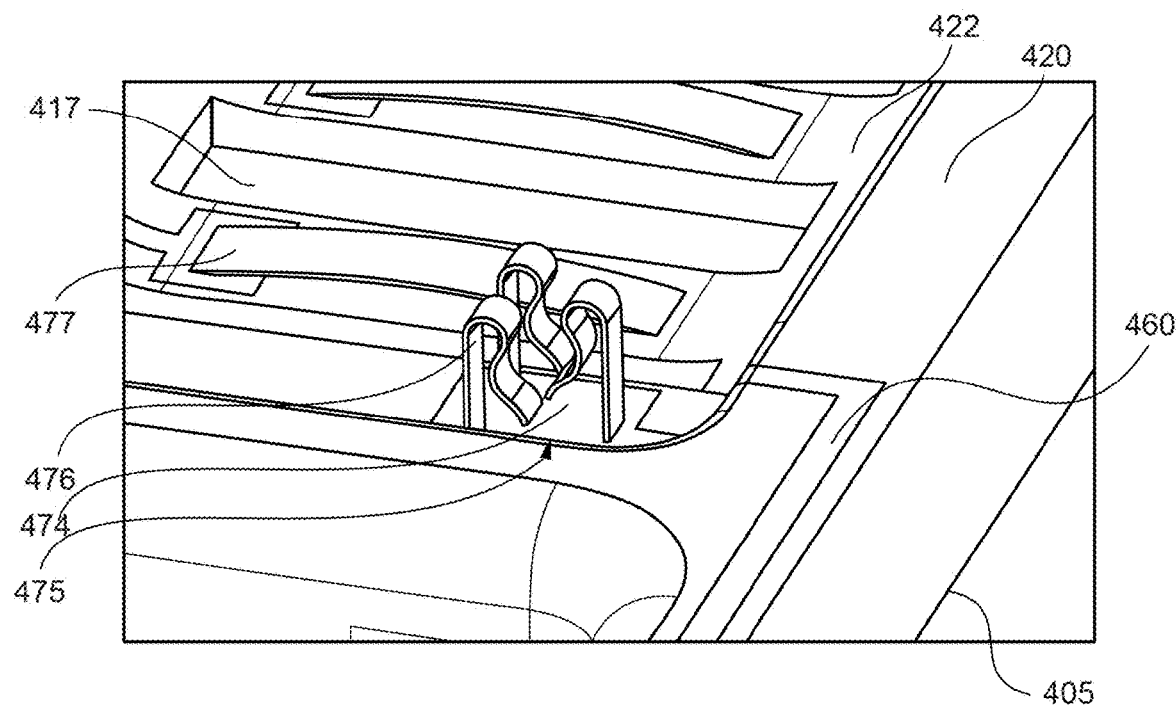
FIG. 4E shows a perspective view of an electrical contact of FIG. 4C.
Figure 4F:
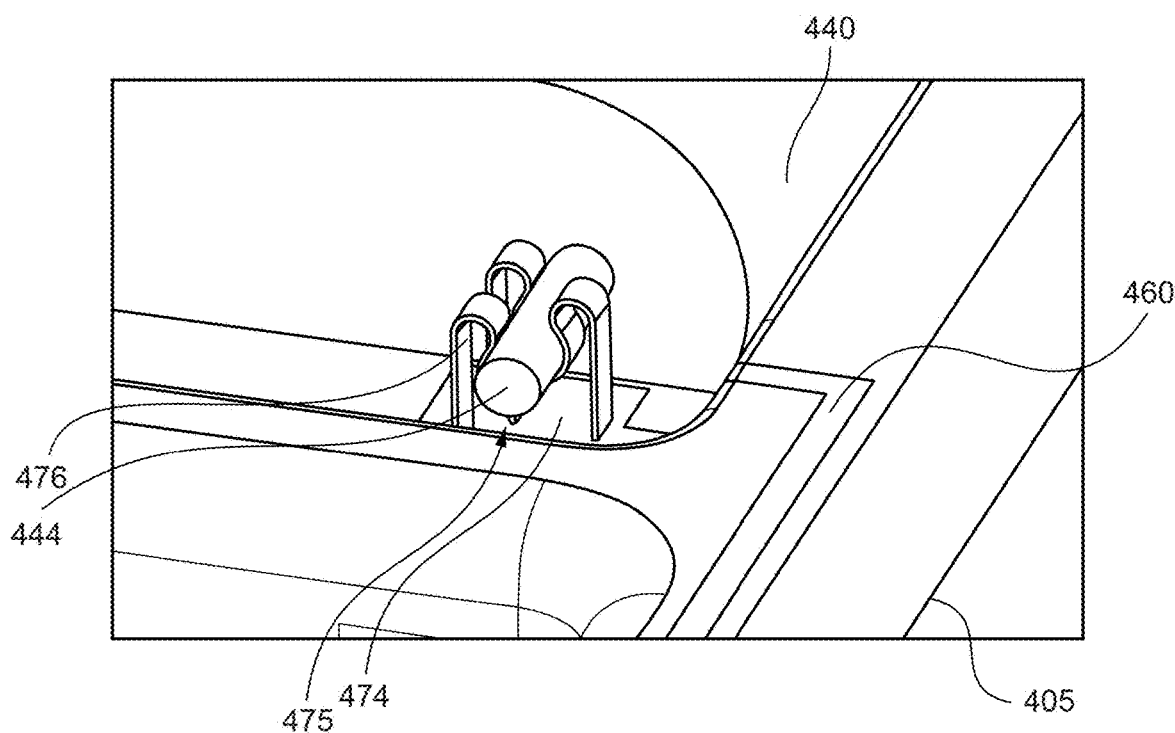
FIG. 4F shows a perspective view of the electrical contact of FIG. 4E further including a battery pin.

FIG. 4E shows a perspective view of electrical contact 475 of FIG. 4C in greater detail. Electrical connection 475 has two or more connectors 476 to form an array of connectors for securing a battery pin (pin 444 as shown in FIG. 4F). Connectors 476 may be made of sheet metal strips, for example, and directly embedded, press fit, or overmolded into nest portion 405. Electrical connection 475 further includes metallized portion 474 to make a trace to connect with electrical interconnect 460. FIG. 4F shows a perspective view of the electrical connection of FIG. 4E further including a battery pin 444. Battery pin 444 is secured in the array of connectors 476. The array of connectors 476 provides a spring loaded force to retain pin 444 mechanically as well as ensuring a solid electrical connection.

Figure 4G:
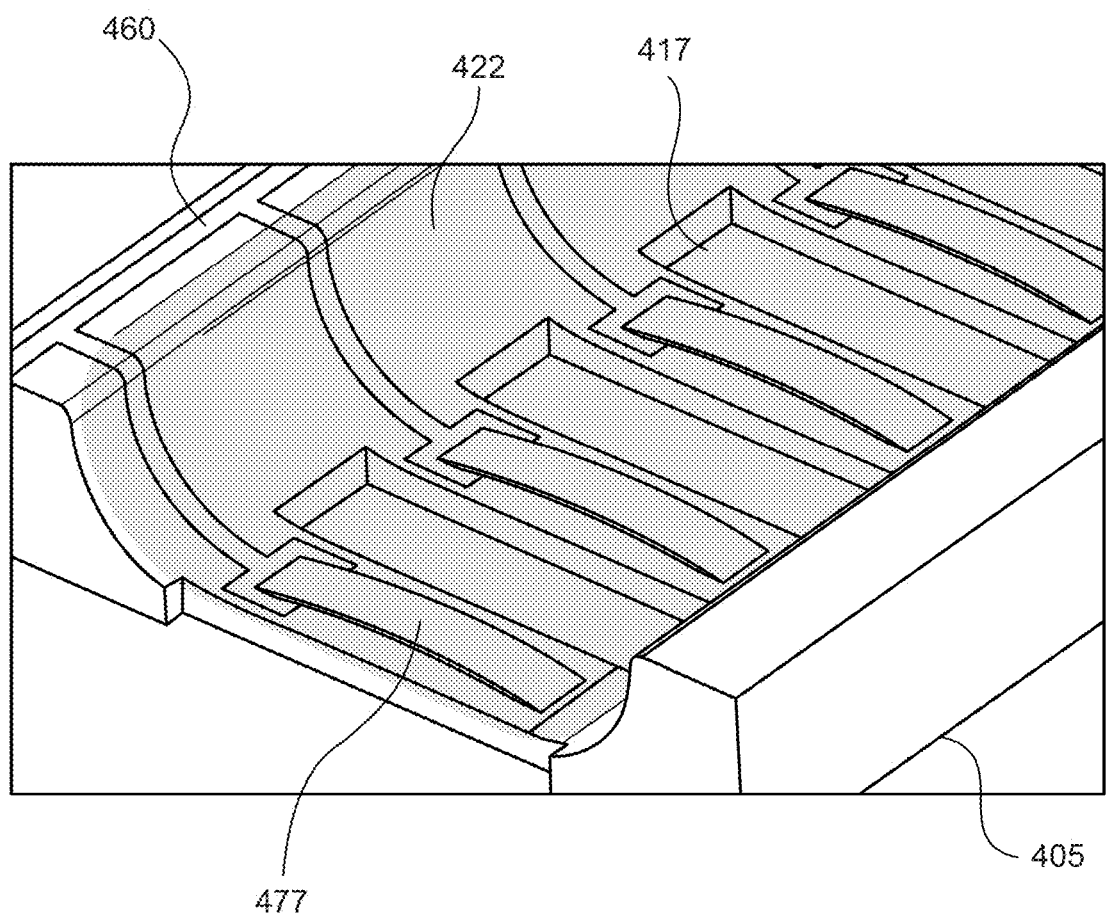
FIG. 4G shows a perspective view of other electrical connections including leaf spring type connections of FIG. 4C.

FIG. 4G shows a perspective view of the electrical connections 477 of FIG. 4C in greater detail. Electrical connections 477 may be leaf spring type connections as shown. The one or more leaf spring connections 477 contact to power source body 442 (as shown in FIG. 4D). Electrical connections 477 may be mounted to flat, curved (as in portion 422), or angled faces to more securely hold power source 440 securely.

Figure 4H:
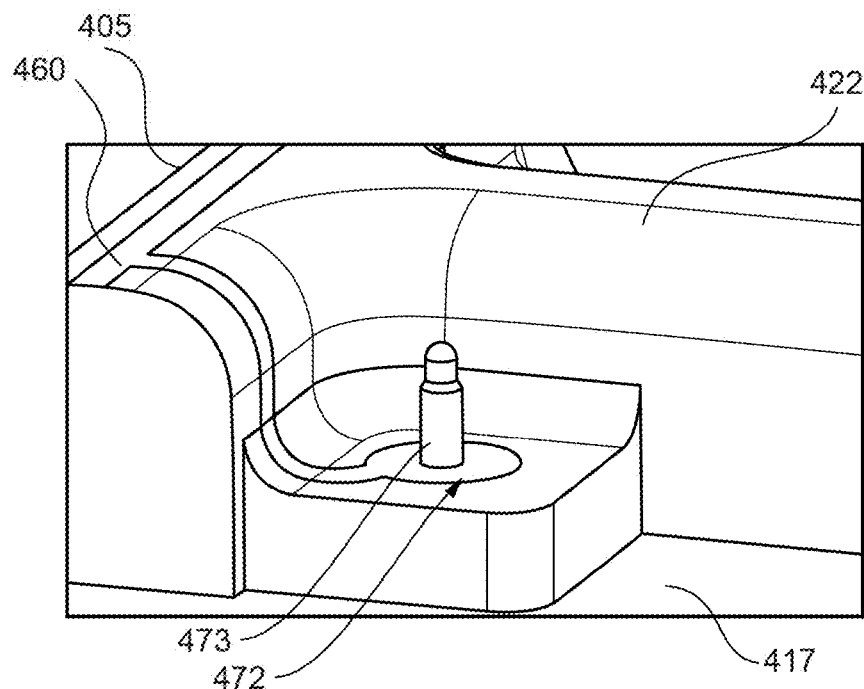
FIG. 4H shows a perspective view of other electrical connections including pogo pin type connections of FIG. 4C.
Figure 4I:
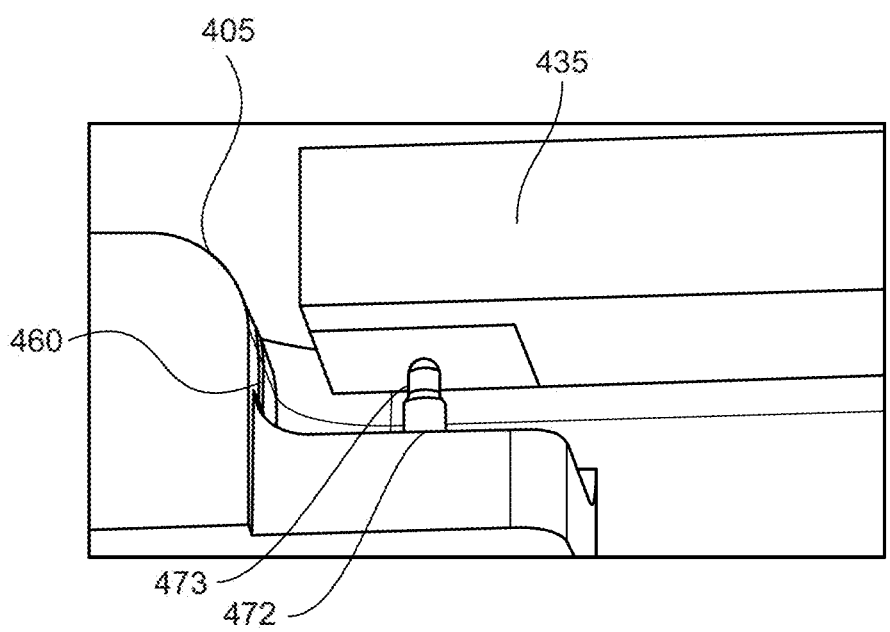
FIG. 4I shows the electrical connection of FIG. 4H engaging with the electronics module (as in FIG. 4D).

FIG. 4H shows a perspective view of the electrical connections 472 of FIG. 4C in greater detail. Electrical connections 472 may be pogo pin type connections as shown with pin portion 473 extending into the interior of components cavity 430. As shown in FIG. 4I, electrical connections 472 engage with the electronics module 435 of FIG. 4D.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A medical device comprising:
  a first nest portion;
  a second nest portion mateable with the first nest portion to form a nest housing, wherein the nest housing comprises an interior surface and an exterior surface;
  a component cavity defined by the interior surface;
  an electronics module disposed within a first region of the component cavity, wherein the electronics module comprises a processor;
  a power source disposed within a second region of the component cavity;
  an electrical interconnect formed on or embedded within the first nest portion, the second nest portion, or a combination thereof, wherein the electrical interconnect electrically connects the electronics module to the power source; and
  a casing formed around the nest housing to completely enclose the nest housing.

2. The medical device of claim 1, further comprising:
  a first electrical contact disposed between the electrical interconnect and the electronics module; and
  a second electrical contact disposed between the electrical interconnect and the power source,
  wherein the nest housing provides a force on the first electrical contact and the second electrical contact to maintain electrical connection between the electronics module and the power source via the first electrical contact, the second electrical contact, and the electrical interconnect.

3. The medical device of claim 2, wherein the first electrical contact and the second electrical contact are formed on or embedded within the first nest portion, the second nest portion, or a combination thereof, and the first electrical contact and the second electrical contact are a spring clip, a pogo pin, a contact pad, or a combination thereof.

4. The medical device of claim 1, wherein the casing is formed of a bioceramic, bioglass, or titanium.

5. The medical device of claim 4, further comprising a layer of compliant material disposed between the nest housing and the casing.

6. The medical device of claim 2, further comprising:
  a first fit component disposed between the first nest portion, the second nest portion, or a combination thereof and the electronics module; and
  a second fit component disposed between the first nest portion, the second nest portion, or a combination thereof and the power source,
  wherein the first fit component and the second fit component provide force on the electronics module and the power source, respectively, to maintain electrical connection between the electronics module and the power source via the first electrical contact, the second electrical contact, and the electrical interconnect.

7. The medical device of claim 1, further comprising:
a cap fixed to the nest housing; and
one or more feedthroughs that pass through the cap, wherein the electronics module is electrically connected to the one or more feedthroughs.

8. The medical device of claim 1, wherein the first nest portion, the second nest portion, or a combination thereof comprise one or more layers of dielectric material and the electrical interconnect is formed on or embedded within the one or more layers of dielectric material.

9. The medical device of claim 8, wherein the dielectric material is a polyimide, a liquid crystal polymer (LCP), parylene, polyether ether ketone (PEEK), or a combination thereof.

10. The medical device of claim 8, wherein the electrical interconnect comprises a conductive material and the conductive material is copper (Cu), gold (Au), silver (Ag), gold/chromium (Au/Cr), platinum (Pt), platinum/iridium (Pt/Ir), titanium (Ti), gold/titanium (Au/Ti), or any alloy thereof.

11. The medical device of claim 8, wherein the electronics module further comprises non-transitory machine readable storage medium having instructions stored thereon that when executed by the processor cause the processor to perform one or more operations.

12. The medical device of claim 8, wherein the electronics module is a printed circuit board assembly (PCBA).

13. The medical device of claim 12, wherein the PCBA is formed on the one or more layers of dielectric material.

14. The medical device of claim 8, further comprising:
an antenna; and
another electrical interconnect formed on or embedded within the one or more layers of dielectric material, wherein the another electrical interconnect electrically connects the antenna to the electronics module or the power source.

15. The medical device of claim 14, wherein the antenna is a wireless charging antenna or a wireless communication antenna.

16. The medical device of claim 14, wherein the antenna is disposed within a third region of the component cavity.

17. The medical device of claim 8, wherein the electrical interconnect is a wire, a drawn filled tube, a helical coiled conductor, a microwire, a conductive metal trace, or a printed circuit.

18. A medical device comprising:
an implantable neurostimulator including:
a nest housing comprising an interior surface and an exterior surface;
a component cavity defined by the interior surface;
an electronics module disposed within a first region of the component cavity, wherein the electronics module comprises a processor and a pulse generator;
a power source disposed with a second region of the component cavity;
an electrical interconnect formed on or embedded within a portion of the nest housing, wherein the electrical interconnect electrically connects the electronics module to the power source;
a casing formed around the nest housing to completely enclose the nest housing;
a cap fixed to the nest housing; and
one or more feedthroughs that pass through the cap, wherein the electronics module is electrically connected to the one or more feedthroughs; and
a lead assembly including:
a lead body including a conductor material;
a lead connector that connects the conductor material to the one or more feedthroughs; and
one or more electrodes connected to the conductor material.

19. The medical device of claim 18, wherein the implantable neurostimulator further includes:
a first electrical contact disposed between the electrical interconnect and the electronics module; and
a second electrical contact disposed between the electrical interconnect and the power source,
wherein the nest housing provides a force on the first electrical contact and the second electrical contact to maintain electrical connection between the electronics module and the power source via the first electrical contact and the second electrical contact.

20. A medical device comprising:
a nest housing comprising one or more layers of dielectric material, wherein the one or more layers of dielectric material form an interior surface and an exterior surface of the nest housing;
a component cavity defined by the interior surface;
a first electronic component disposed within the component cavity;
a second electronic component disposed within the component cavity;
an electrical interconnect formed on or embedded within the one or more layers of dielectric material;
a casing formed around the nest housing to completely enclose the nest housing;
a first electrical contact disposed between the electrical interconnect and the first electronic component; and
a second electrical contact disposed between the electrical interconnect and the second electronic component,
wherein the electrical interconnect electrically connects the first electronic component and the second electronic component via the first electrical contact and the second electrical contact.

* * * * *